US010546207B2

(12) United States Patent
Sundaresan et al.

(10) Patent No.: US 10,546,207 B2
(45) Date of Patent: Jan. 28, 2020

(54) NORMALIZED DEFECT CHARACTERIZATION OF PULSE THERMOGRAPHIC NONDESTRUCTIVE EVALUATION

(71) Applicant: North Carolina Agricultural and Technical State University, Greensboro, NC (US)

(72) Inventors: Mannur J. Sundaresan, Greensboro, NC (US); Letchuman Sripragash, Greensboro, NC (US)

(73) Assignee: North Carolina Agricultural and Technical State University, Greensboro, NC (US)

( * ) Notice: Subject to any disclaimer, the term of this patent is extended or adjusted under 35 U.S.C. 154(b) by 4 days.

(21) Appl. No.: 15/482,851

(22) Filed: Apr. 10, 2017

(65) Prior Publication Data

US 2017/0294013 A1    Oct. 12, 2017

Related U.S. Application Data

(60) Provisional application No. 62/320,759, filed on Apr. 11, 2016.

(51) Int. Cl.
*G06K 9/46* (2006.01)
(52) U.S. Cl.
CPC ................. *G06K 9/4604* (2013.01)
(58) Field of Classification Search
CPC .............. G06T 7/0008; G06K 9/4604
See application file for complete search history.

(56) References Cited

U.S. PATENT DOCUMENTS

| 6,516,084 | B2 | 2/2003 | Shepard |
| 6,751,342 | B2 | 6/2004 | Shepard |
| 7,554,086 | B2 | 6/2009 | Shepard et al. |
| 7,699,521 | B2 | 4/2010 | Shepard |
| 7,724,925 | B2 | 5/2010 | Shepard |

(Continued)

OTHER PUBLICATIONS

Balageas, D. L. (2012). Defense and illustration of time-resolved pulsed thermography for NDE. Quantitative Infrared Thermography Journal, 9(1), 3-32. doi: 10.1080/ 17686733.2012.676902.

(Continued)

*Primary Examiner* — Joseph W Becker
(74) *Attorney, Agent, or Firm* — Fox Rothschild LLP

(57) ABSTRACT

A method of thermographic nondestructive evaluation may include heating a portion of a surface of an object from a first surface temperature to a second surface temperature that is greater than the first surface temperature, collecting a plurality of thermal images of the portion of the surface of the object, detecting the sound zone of the portion of the surface of the object, determining a characteristic time corresponding to a time after the heating of the portion of the surface of the object wherein the sound zone of the surface of the object approaches a steady state temperature, normalizing temperature data of the plurality of thermal images with respect to the characteristic time and the steady state temperature, and detecting the defect zone based on differences between normalized temperature data of pixels of the defect zone and normalized temperature data of pixels of the sound.

19 Claims, 13 Drawing Sheets

(56) References Cited

U.S. PATENT DOCUMENTS

| | | | |
|---|---|---|---|
| 7,787,114 B2* | 8/2010 | Wolters | G01N 21/4738 250/205 |
| 7,907,762 B2* | 3/2011 | Ramsay | G06K 9/6224 348/125 |
| 8,204,294 B2* | 6/2012 | Alloo | G01N 25/72 382/141 |
| 8,449,176 B2 | 5/2013 | Shepard | |
| 2002/0128797 A1* | 9/2002 | Sun | G01B 11/06 702/172 |

OTHER PUBLICATIONS

Ibarra-Castanedo, C., Genest, M., Servais, P., Maldague, X. P. V., & Bendada, A. (2007). Qualitative and quantitative assessment of aerospace structures by pulsed thermography. Nondestructive Testing and Evaluation, Sep. 22, 199-215. doi: 10.1080/10589750701448548.

Omar, M., Hassan, M. I., Saito, K., & Alloo, R. (2005). IR self-referencing thermography for detection of in-depth defects. Infrared Physics and Technology, 46, 283-289. doi: 10.1016/j.infrared.2004.04.005.

Shepard, S. M. (2001). Advances in pulsed thermography. In Thermosense XXIII (vol. 4360, pp. 511-515). International Society for Optics and Photonics. doi:10.1117/12.421032.

Shepard, S. M., Lhota, J. R., Rubadeux, B. A, Wang, D., & Ahmed, T. (2003). Reconstruction and enhancement of active thermographic image sequences. Optical Engineering, 42(5), 1337-1342. doi: 10.1117/1.1566969.

Sripragash, L., Smith, C., Kumaran, G., & Sundaresan, M. (Apr. 2013). Monitoring damage development around stress raisers in carbon/epoxy laminates. In Nondestructive Characterization for Composite Materials, Aerospace Engineering, Civil Infrastructure, and Homeland Security 2013(vol. 8694, p. 869404). International Society for Optics and Photonics. doi:10.1117/12.2009858.

* cited by examiner

NORMALIZED DEFECT CHARACTERIZATION OF PULSE THERMOGRAPHIC NONDESTRUCTIVE EVALUATION

CROSS-REFERENCE TO RELATED APPLICATIONS

This application claims priority under 35 U.S.C. § 120 to U.S. Provisional Application Ser. No. 62/320,759, entitled NORMALIZED DEFECT CHARACTERIZATION OF PULSE THERMOGRAPHIC NONDESTRUCTIVE EVALUATION, filed in the USPTO on Apr. 11, 2016, the disclosure of which is incorporated herein by reference in its entirety.

STATEMENT OF GOVERNMENT INTEREST

This invention was developed under government Contract No. NNX09AV08 awarded by National Aeronautics and Space Administration. The U.S. Government has certain rights in this invention.

BACKGROUND

The present invention relates to nondestructive inspection, and in particular, to methods of pulse thermographic nondestructive evaluation of subsurface defects.

Thermographic nondestructive evaluation (TNDE) is a nondestructive evaluation technique that may be capable of evaluating large areas of structures in a relatively short duration of time to detect and/or quantify sub surface defects. TNDE may be used, for example, in aerospace and other applications to detect and measure the extent of damage to structural materials including, for example, carbon epoxy composites. TNDE techniques may include active and passive thermographic techniques. Active thermography includes an external source of heat that may be applied to an object while passive thermography may use heat generated within the object. Pulse thermography, an active thermographic technique, includes a pulse of heat energy that may be applied to the surface of the test object, usually by a flash lamp. The heat energy may cause a rise in the temperature of the surface of the test object. Following this temperature rise, the rate of change of temperature across the surface as a function of time may be monitored using an infrared camera. In a defect free sample, the heat may diffuse through a thickness of the object, resulting in an asymptotic drop in temperature across the surface. However, in areas where there are defects, the diffusion of heat through the thickness may be obstructed, leaving the surface in areas including defects warmer than in defect free areas. The variation of temperature versus time may be used to evaluate defects.

Some TNDE techniques may require quantification of multiple unknowns, including thermal diffusivity of the material, lateral dimension and depth of defects, thickness of the part being inspected, and/or the amount of heat absorbed by the part from the flash. In some techniques, reliable calibration specimens may facilitate the characterization of the defects. The existence of defects may be qualitatively seen in raw thermographic images. Quantitative information can be obtained with additional image processing techniques, including pixel based and image based techniques. Pixel based techniques may evaluate the temperature evolution of a single pixel or point on the surface. Image based techniques may evaluate the thermal contrast of the entire image per time frame.

Some TNDE techniques may include one or more difficulties in evaluating defects. For example, a thermal camera may introduce noise that may be of the same order as temperature differences to be measured, particularly if a defect is located deep inside the material. A flash heating may not heat the surface uniformly. It may be difficult to detect defect free locations to compare to the locations including defects.

In some TNDE techniques, it may be difficult to generate numerical simulations that compare with the experimental results. For example, the thermo-mechanical properties of the subject material may not be available. Moreover differences in the amounts of heat absorbed, the ambient temperature, the thickness of the sample, etc. may yield differences between the experimental results and the numerical simulations that may make it difficult to evaluate defects.

SUMMARY

According to some embodiments of the inventive concepts, methods of thermographic nondestructive evaluation may be provided. A method of thermographic nondestructive evaluation may include heating a portion of a surface of an object from a first surface temperature to a second surface temperature that is greater than the first surface temperature. The portion of the surface of the object may include a defect zone including a defect that is below the surface of the object and comprising a sound zone. The method may include collecting a plurality of thermal images of the portion of the surface of the object, the plurality of thermal images may include a series of further thermal images that correspond to times at intervals beginning with a first time. The first time may be a time before the portion of the surface of the object is heated. The method may include detecting the sound zone of the portion of the surface of the object. The method may include determining a characteristic time corresponding to a time after the heating of the portion of the surface of the object wherein the sound zone of the surface of the object approaches a steady state temperature. The method may include normalizing temperature data of the plurality of thermal images with respect to the characteristic time and the steady state temperature. The method may include detecting the defect zone based on differences between normalized temperature data of pixels of the defect zone and normalized temperature data of pixels of the sound zone.

BRIEF DESCRIPTION OF THE DRAWINGS

The accompanying drawings, which are incorporated in and constitute a part of the specification, illustrate embodiments of the invention and, together with the description, serve to explain principles of the invention.

Figure 1A:
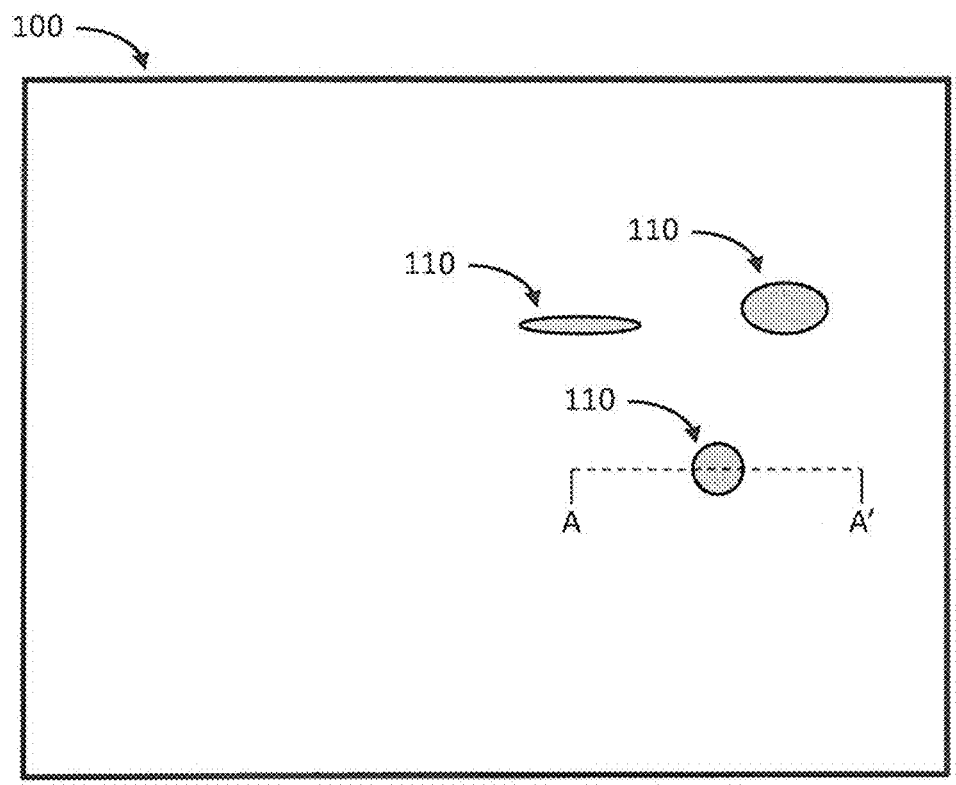
FIG. 1A is a plan view schematically illustrating an object including subsurface defects according to some embodiments of the present invention.
Figure 2A:
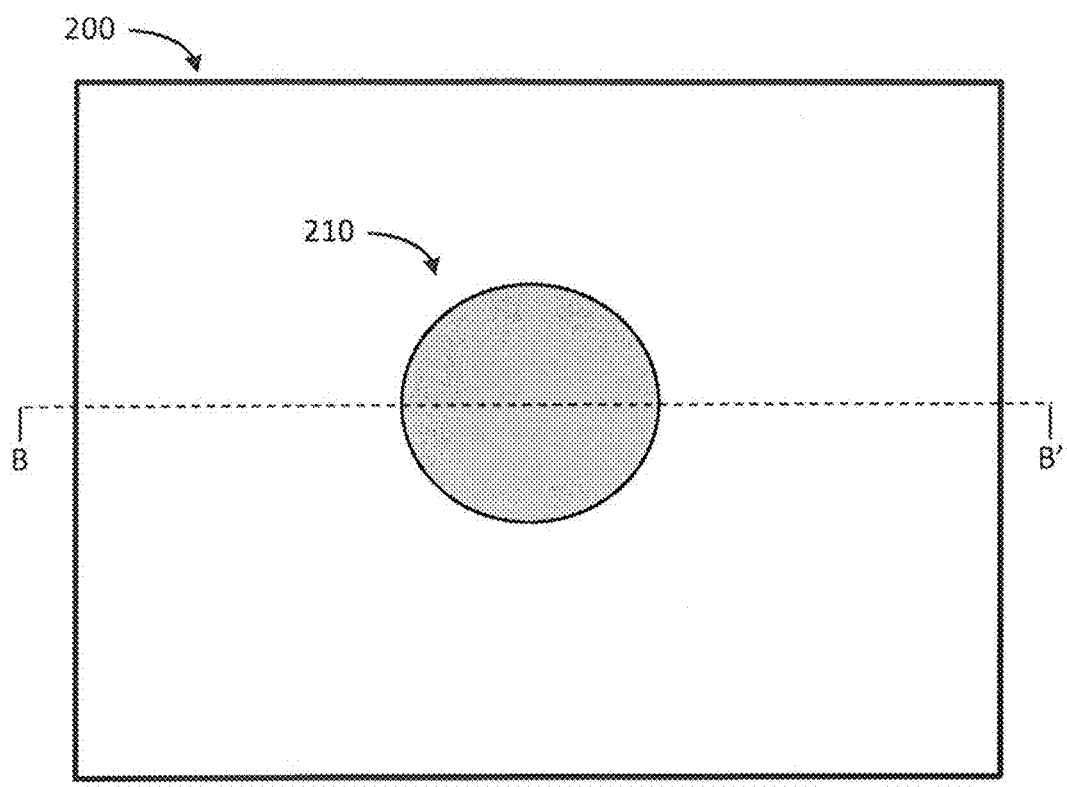

FIG. B is a cross-sectional view taken along the line A-A' of the object of FIG. 1A;

FIG. 2A is a plan view schematically illustrating an object including a symmetrical flat bottom hole defect according to some embodiments of the present invention.

Figure 2B:
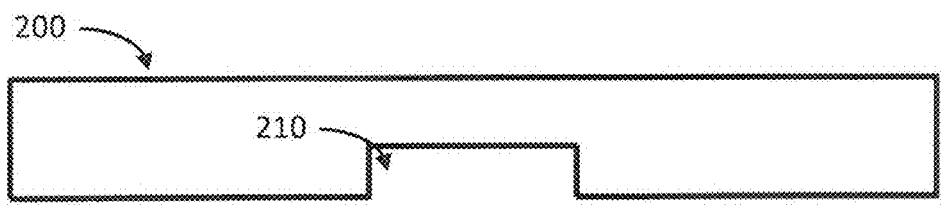
Figure 3:
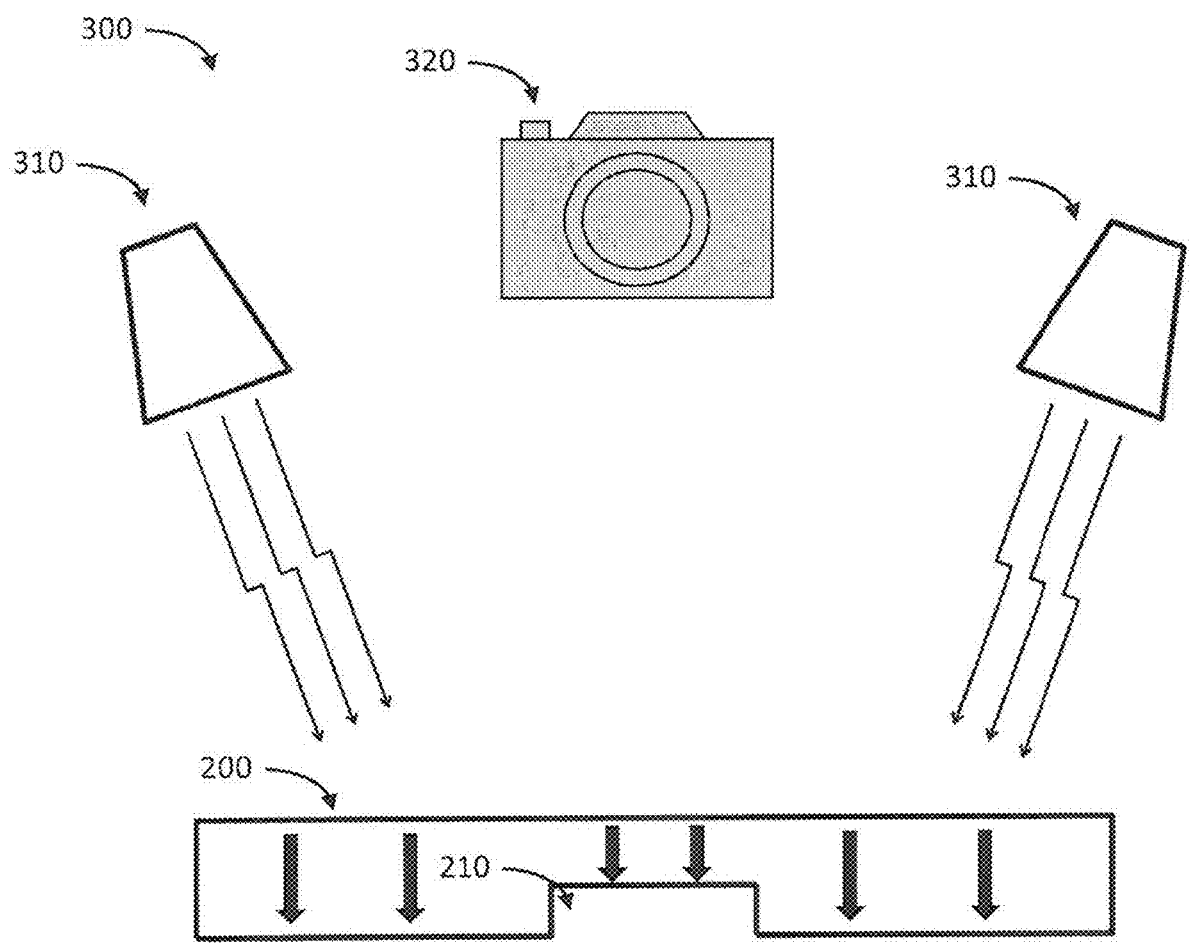

FIG. 2B is a cross-sectional view taken along the line B-B' of the object of FIG. 2A;

FIG. 3 is a cross-sectional view schematically illustrating a system for thermographic nondestructive evaluation according to some embodiments of the present invention.

Figure 4:
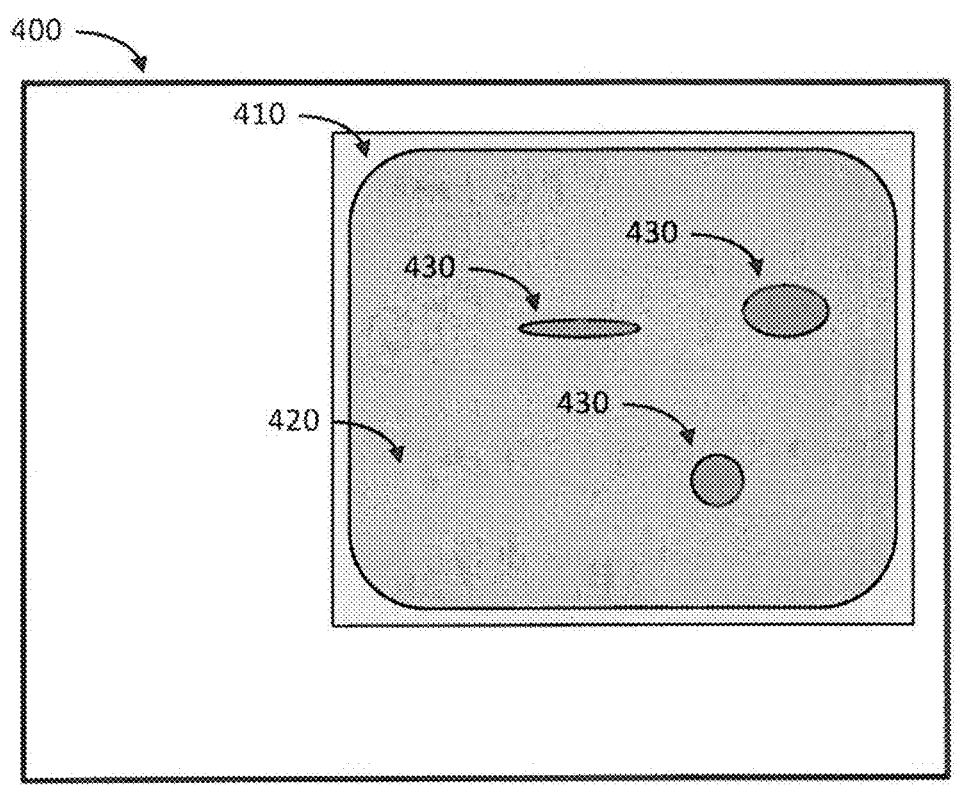

FIG. 4 is a plan view schematically illustrating an object including defects according to some embodiments of the present invention.

Figure 5A:
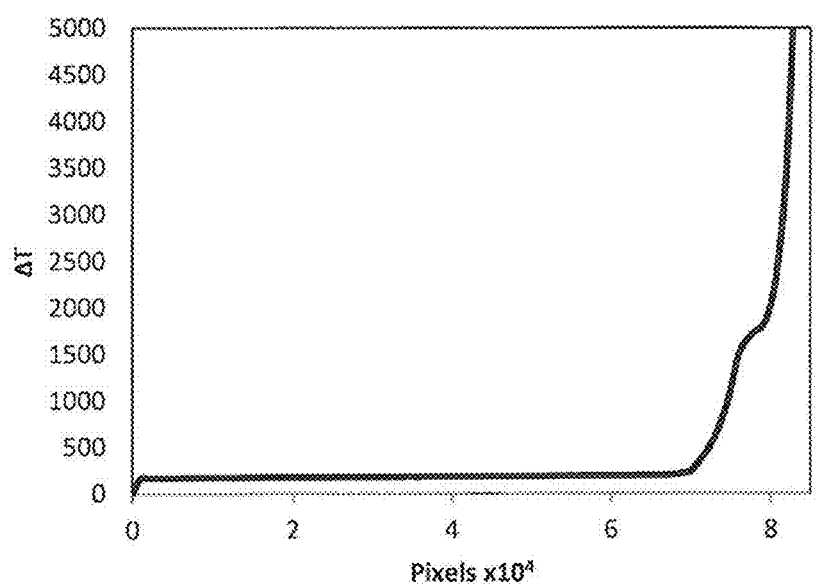
Figure 5B:
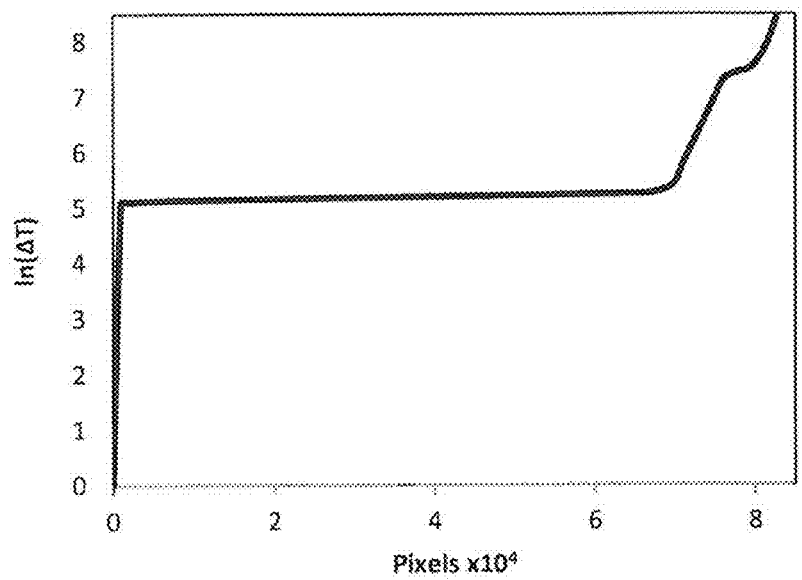

FIGS. 5A and 5B are graphs illustrating a one dimensional array of temperature data of pixels of one frame, according to some embodiments of the present invention.

Figure 6:
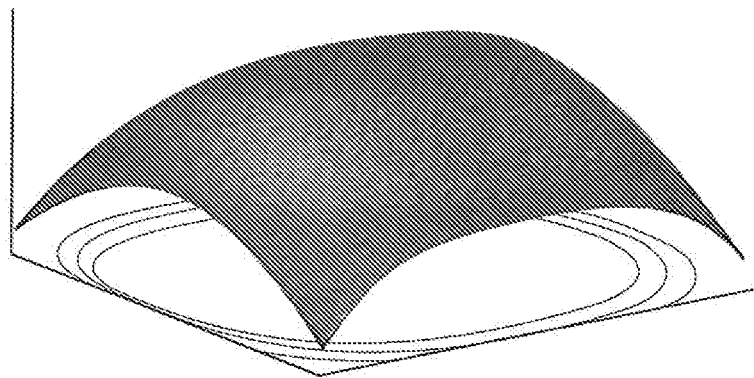

FIG. 6 is a graph of a surface fitted to temperature difference data of a second region according to some embodiments of the present invention.

Figure 7:
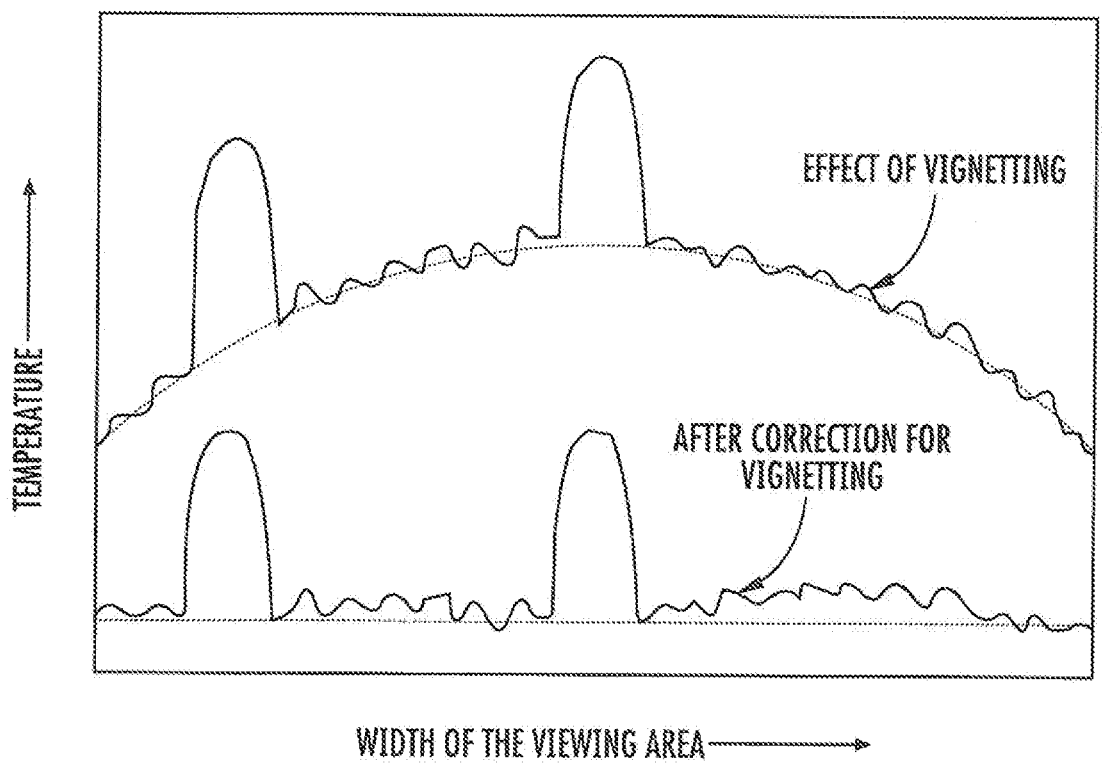

FIG. 7 is a graph illustrating pixel data before and after correcting for vignetting according to some embodiments of the present invention.

Figure 8A:
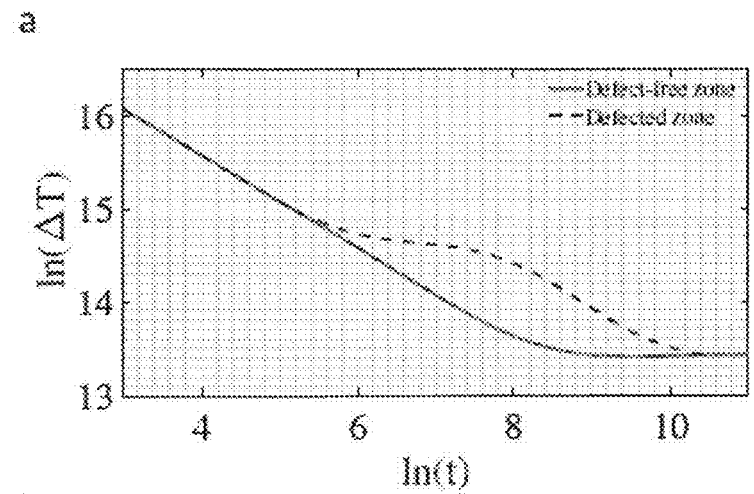
Figure 8B:
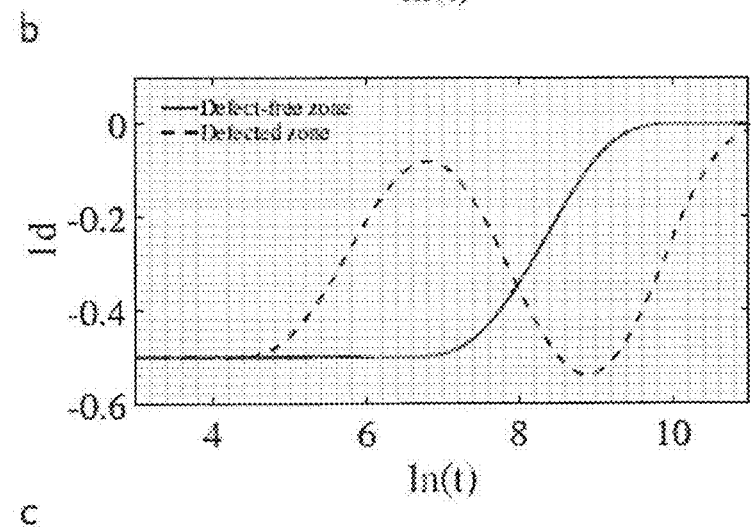
Figure 8C:
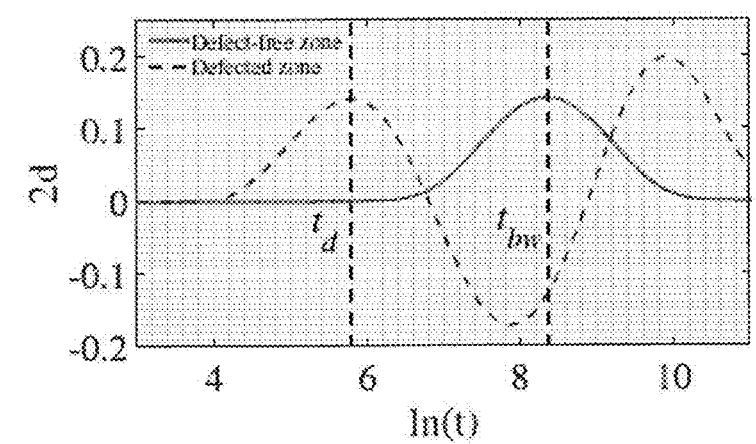

FIGS. 8A, 8B, and 8C are graphs illustrating measured pixel temperature values versus time according to some embodiments of the present invention.

Figure 9A:
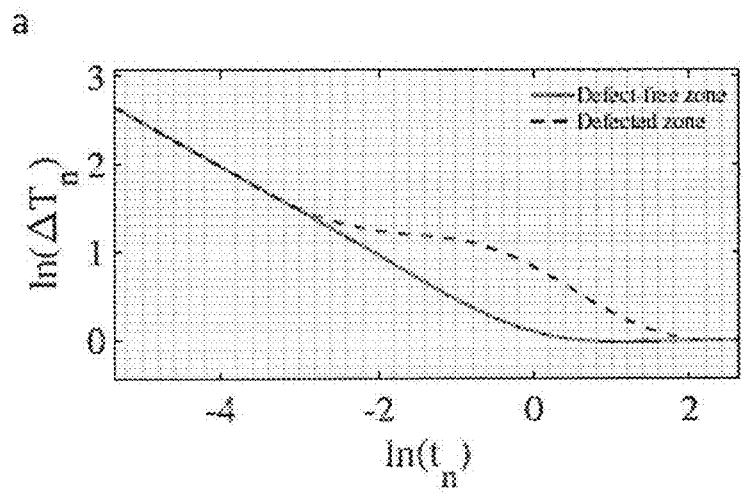
Figure 9B:
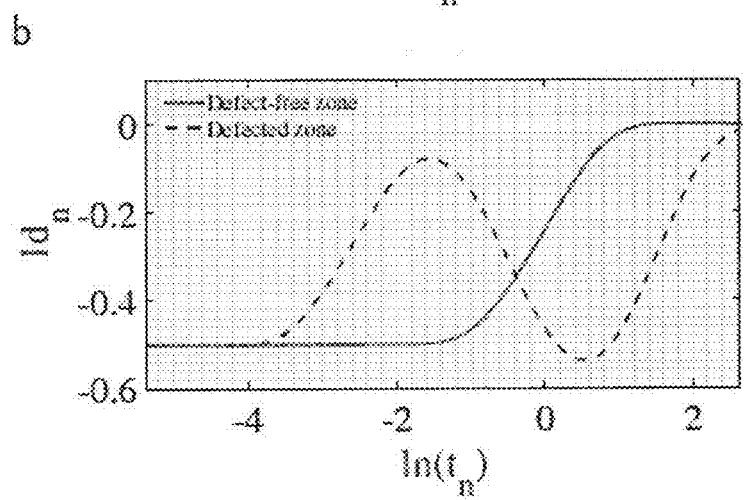
Figure 9C:
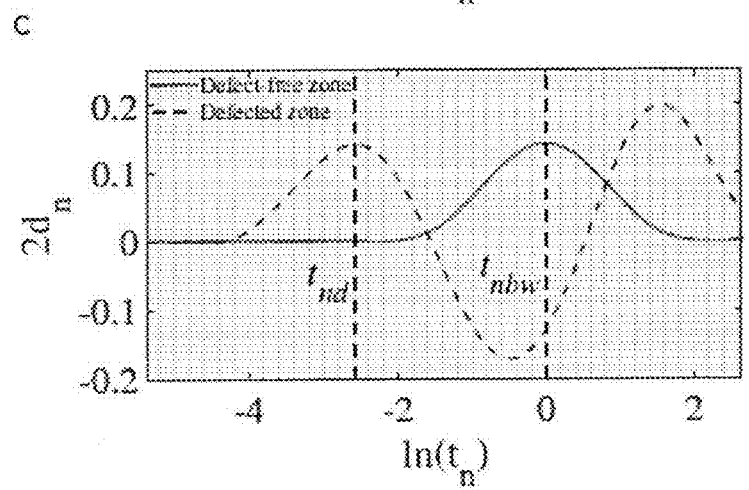

FIGS. 9A, 9B, and 9C are graphs illustrating normalized measured pixel temperature values versus normalized time according to some embodiments of the present invention.

Figure 10:
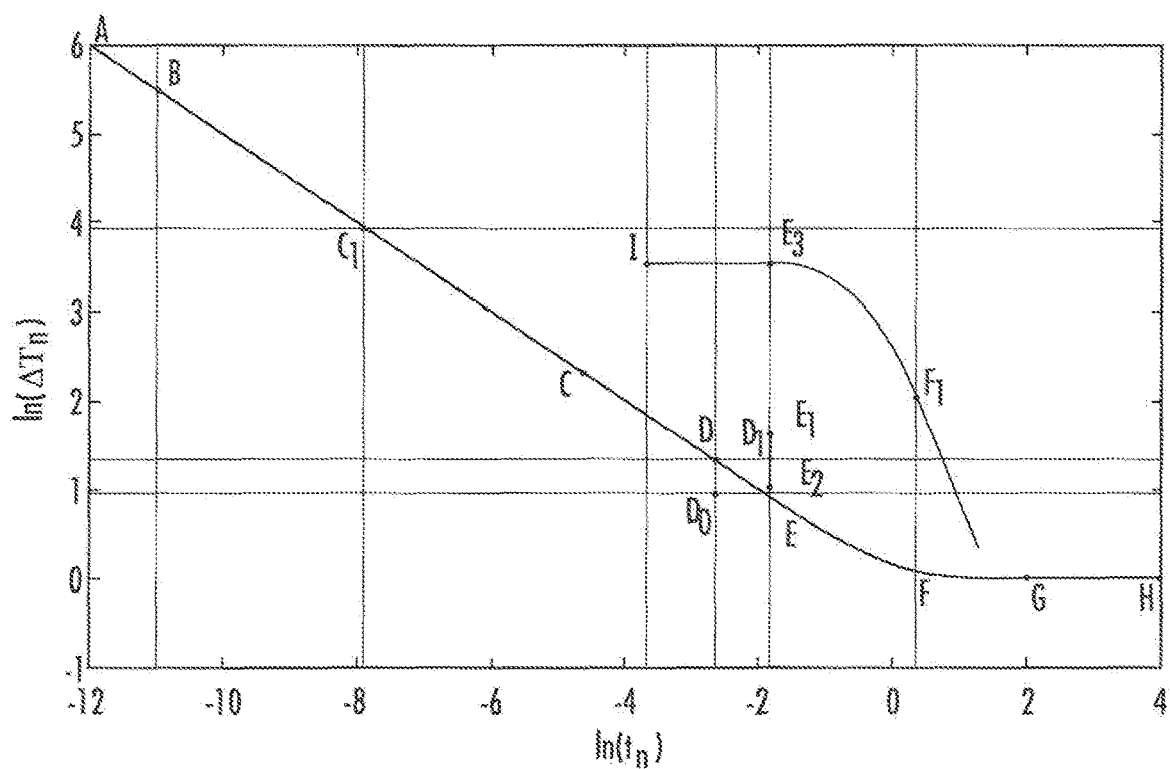

FIG. 10 is a graph illustrating an ideal heat diffusion shown in normalized form according to some embodiments of the present invention.

Figure 11:
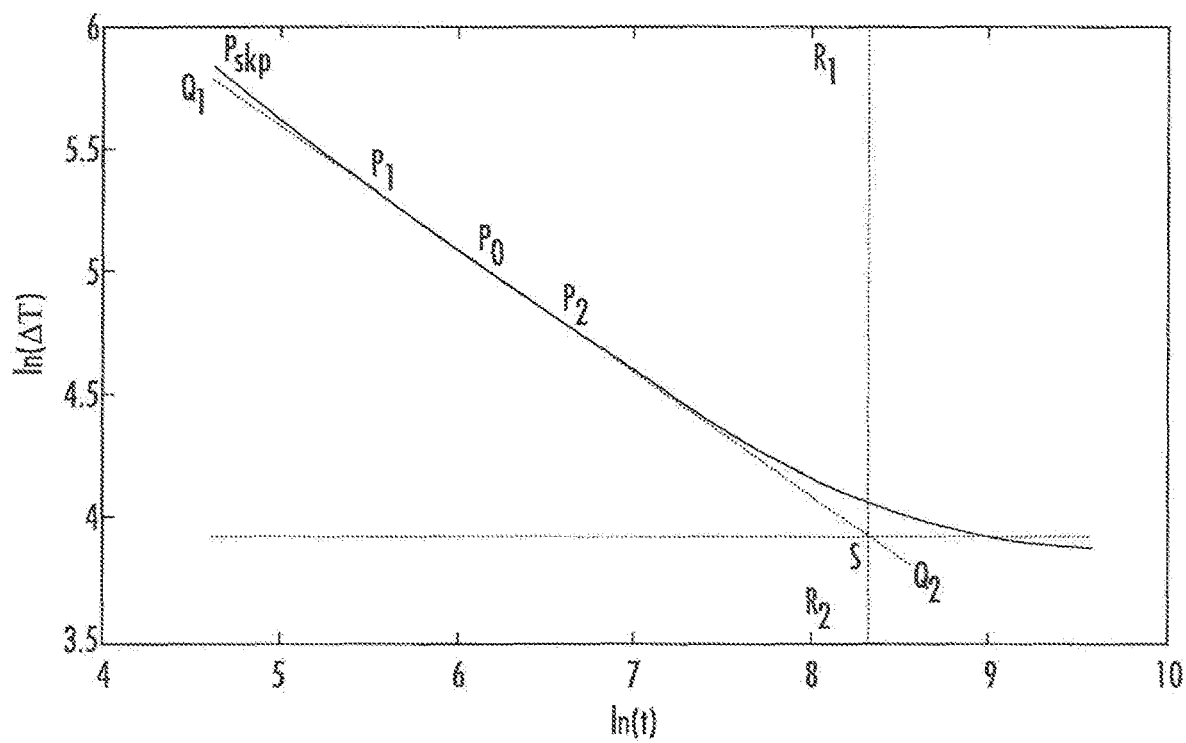

FIG. 11 is a graph illustrating an average of sound zone data according to some embodiments of the present invention.

Figure 12:
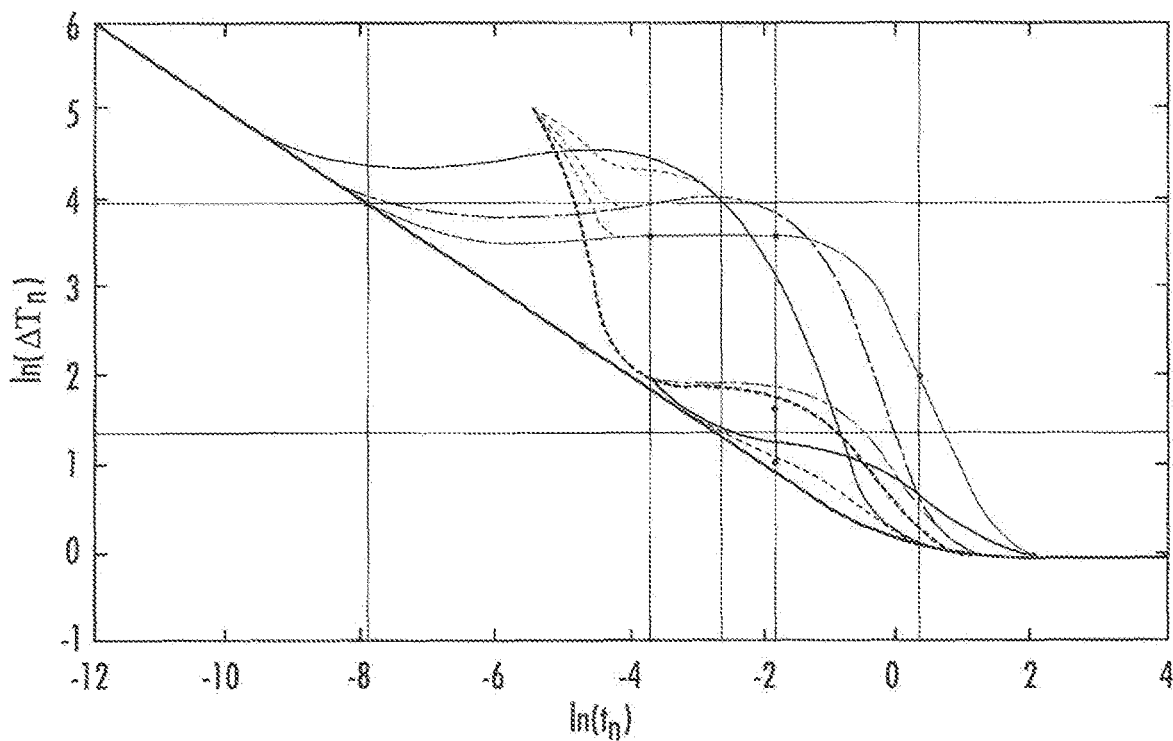

FIG. 12 is a graph illustrating a sample resultant set of curves with raw normalized experimental data according to some embodiments of the present invention.

Figure 13:
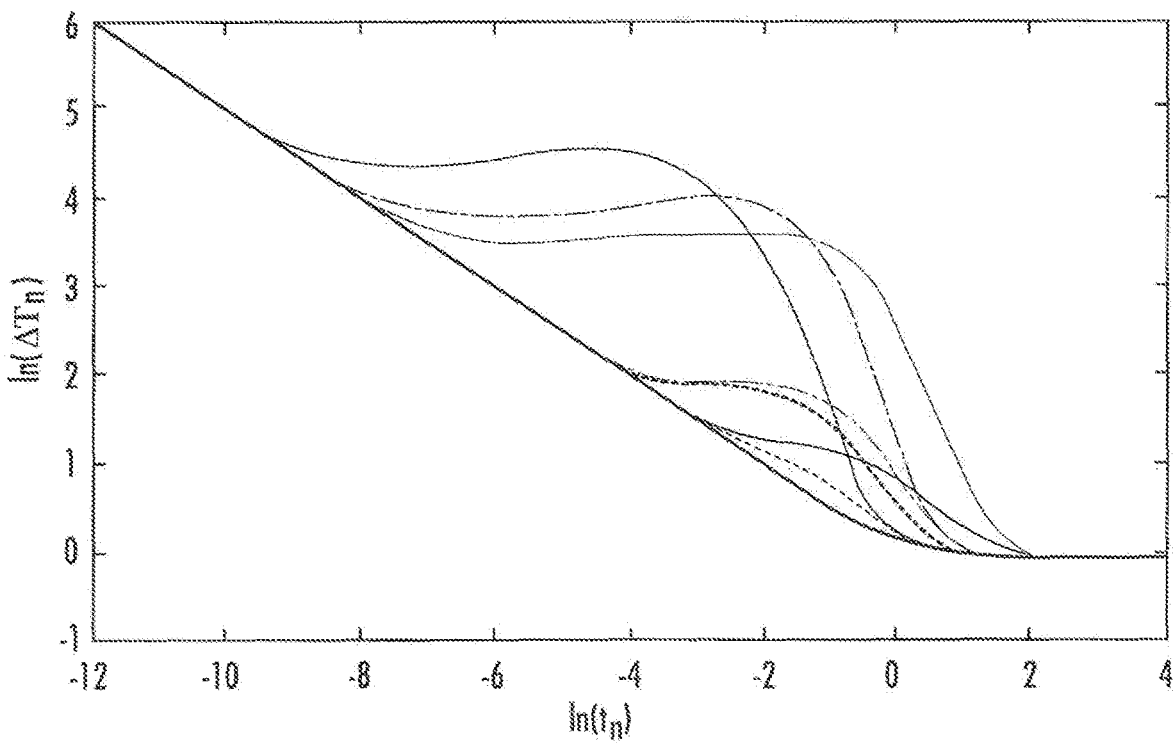

FIG. 13 is a graph illustrating a finalized set of curves according to some embodiments of the present invention.

Figure 14:
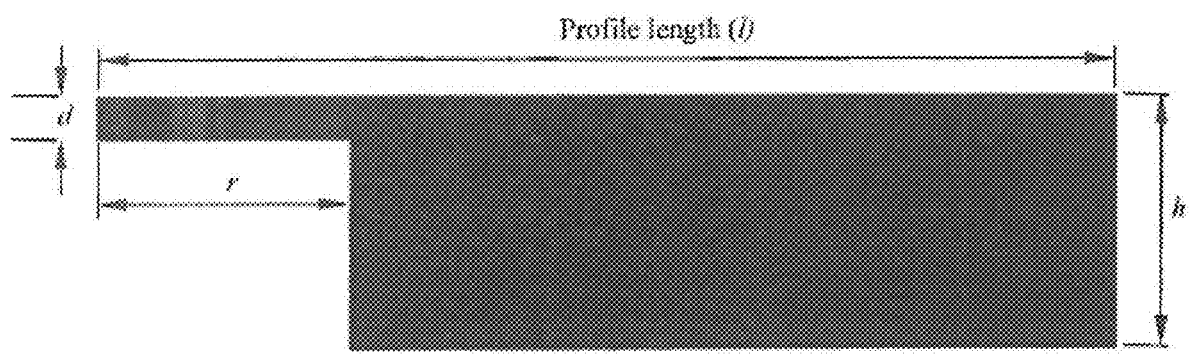

FIG. 14 is a cross-sectional view of an axisymmetrical model according to some embodiments of the present invention.

Figure 15:
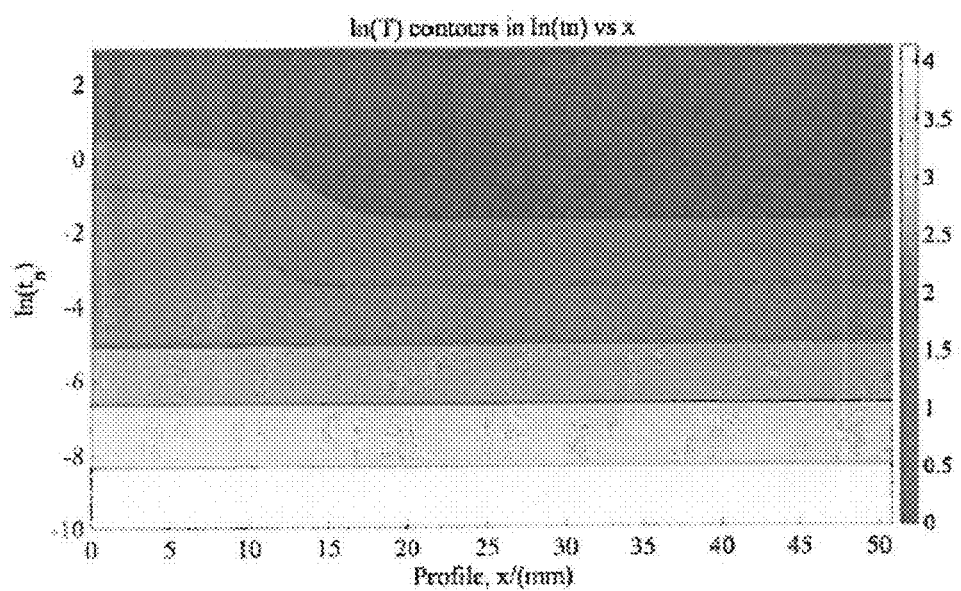
Figure 16:
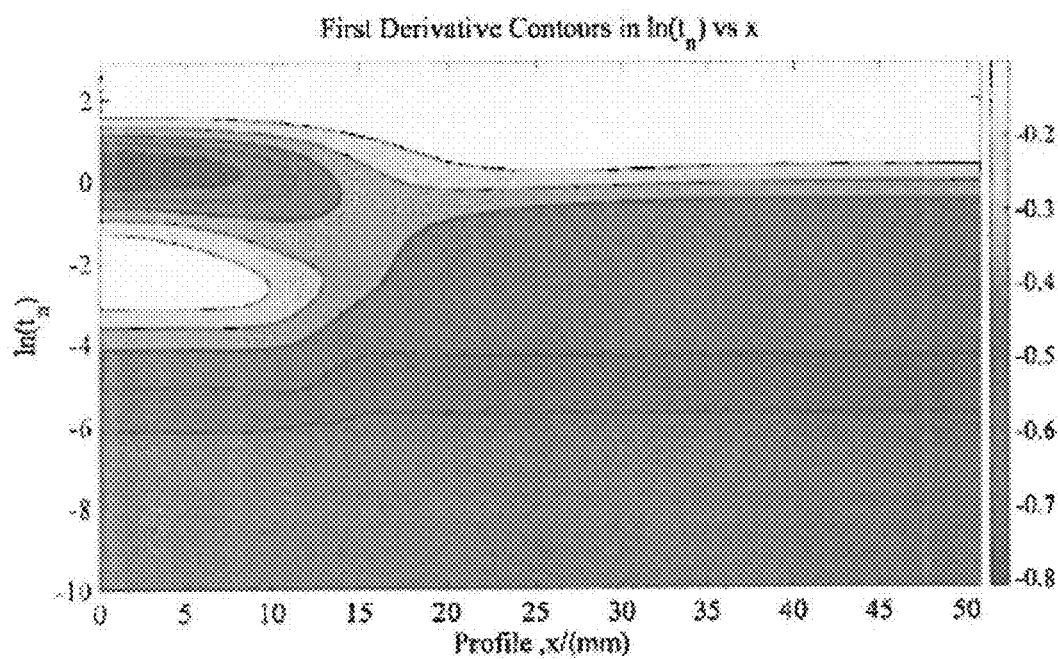
Figure 17:
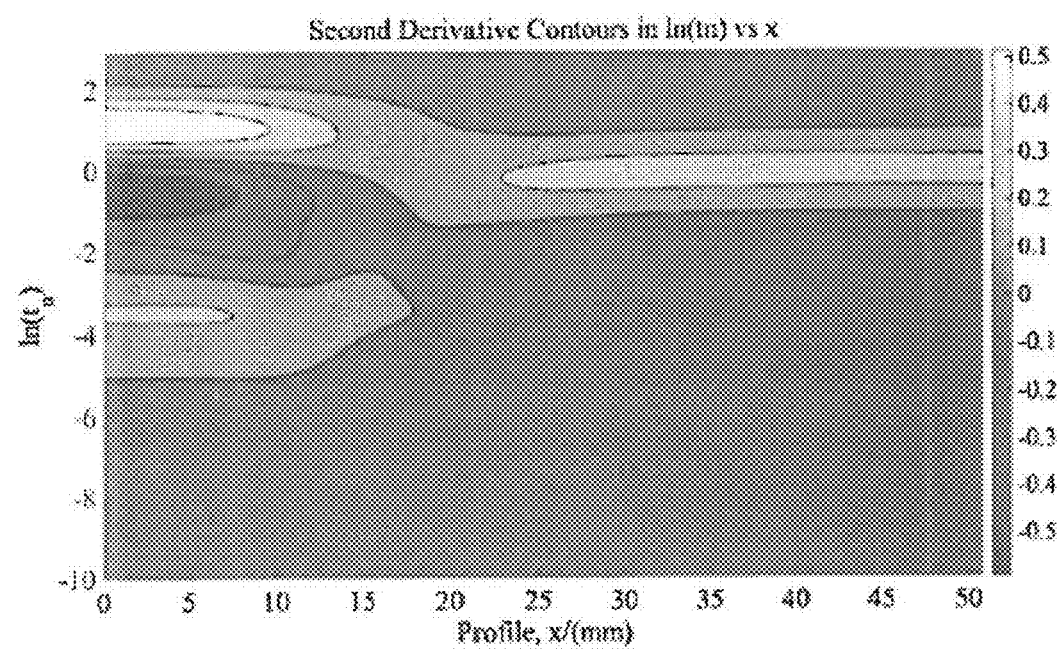

FIGS. 15-17 are three dimensional graphs illustrating contour plots according to some embodiments of the present invention.

Figure 18:
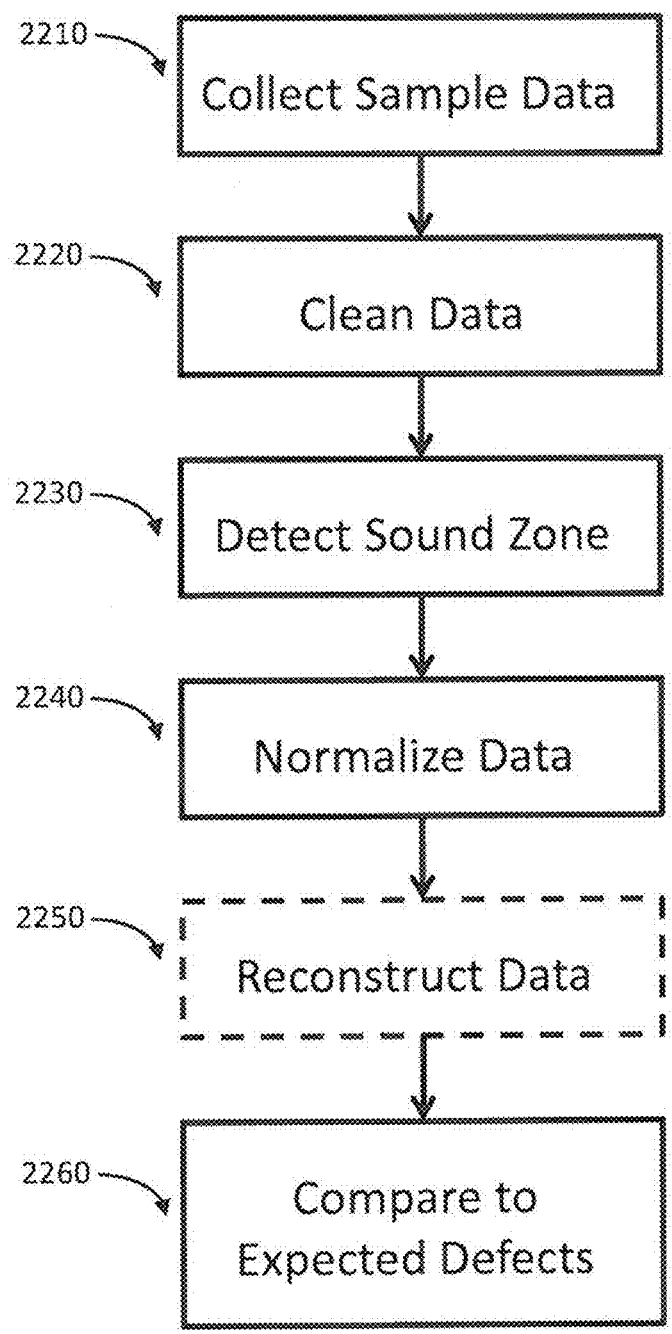

FIG. 18 is a block diagram illustrating steps in methods of evaluating defects according to some embodiments of the present invention.

DETAILED DESCRIPTION OF THE EMBODIMENTS

Embodiments are described in detail with reference to the accompanying drawings. The present invention, however, may be embodied in various different forms, and should not be construed as being limited only to the illustrated embodiments set forth herein. Rather, these embodiments are provided as examples so that this disclosure will be thorough and complete, and will fully convey the concept of the present invention to those skilled in the art. Unless otherwise noted, like reference numerals denote like elements throughout the attached drawings and written description, and thus descriptions may not be repeated.

The terminology used herein is for the purpose of describing particular embodiments only and is not intended to be limiting of the present invention. As used herein, the singular terms "a," "an" and "the" are intended to include the plural forms as well, unless the context clearly indicates otherwise. As used herein, the term "and/or" includes any and all combinations of one or more of the associated listed items.

It will be understood that the terms "comprises", "comprising,", "includes" and/or "including", when used herein, specify the presence of stated features, integers, steps, operations, elements, and/or components, but do not preclude the presence or addition of one or more other features, integers, steps, operations, elements, components, and/or groups thereof. It will be also understood that although the terms first, second, third etc. may be used herein to describe various elements, these elements should not be limited by these terms. These terms are only used to distinguish one element from another element. Thus, a first element in some embodiments could be termed a second element in other embodiments without departing from the teachings of the present invention. Example embodiments of aspects of the present invention explained and illustrated herein include their complementary counterparts. The same reference numerals or the same reference designators denote the same elements throughout the specification.

Unless otherwise defined, all terms (including technical and scientific terms) used herein have the same meaning as commonly understood by one of ordinary skill in the art to which this present invention belongs. It will be further understood that terms, such as those defined in commonly used dictionaries, should be interpreted as having a meaning that is consistent with their meaning in the context of the relevant art and/or the present specification and will not be interpreted in an idealized or overly formal sense unless expressly so defined herein.

Embodiments of the present invention may include a normalization scheme that reduces or eliminates difficulties present in some previous TNDE techniques. As a result of this normalization, it may be feasible to directly obtain estimation of defect depth of a material of a given thickness. With the normalization, results from a validated numerical simulation may be used to generate a thermographic profile corresponding that may be used to evaluate defects with the same defect geometry but are present in a different material. This information may be valuable to decide the experimental settings such as the frame rate needed as well as the energy level from the flash lamp in order to achieve a desirable signal to noise ratio.

Figure 1B:
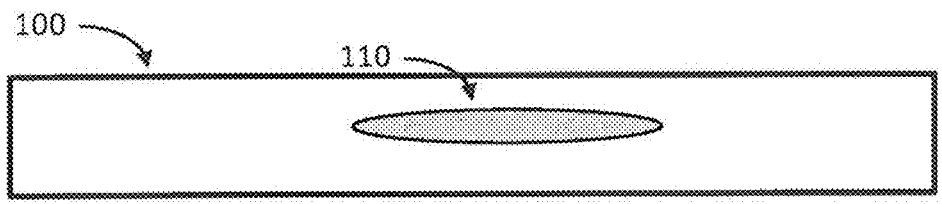

FIG. 1A is a plan view schematically illustrating an object including subsurface defects according to some embodiments of the present invention. FIG. 1B is a cross-sectional view taken along the line A-A' of the object of FIG. 1A. Referring to FIGS. 1A and 1B, an object 100 may include one or more subsurface defects 110. The object 100 may be a composite laminate, a metal sheet, or may include another substance. The object 100 may include a flat surface of substantially uniform thickness. For example, the object 100 may be a structural member of a device used in aerospace or other applications, where it may be important to detect and measure an extent of damage. The defects 110 may be buried below a top surface of the object 100. The defects 110 may not be visible from the top surface of the object 100. In some embodiments, the defects may be of various shapes, sizes, and depths from the top surface of the object 100. The defects 110 may not be uniform or symmetrical.

FIG. 2A is a plan view schematically illustrating an object including a symmetrical flat bottom hole defect according to some embodiments of the present invention. FIG. 2B is a cross-sectional view taken along the line B-B' of the object of FIG. 2A. Referring to FIGS. 2A and 2B, an object 200 may include a defect 210. The object 200 may be similar to the object 100 of FIGS. 1A and 1B except as noted herein. Some descriptions may be omitted for brevity. The object 200 may be a flat plate with a uniform thickness except for the defect 210. The defect 210 may be a flat bottom hole in a bottom surface of the object 200. The defect 210 may be of a uniform round shape of a fixed diameter and with a fixed depth. Although the uniform defect 210 may be used to simplify the description of the invention herein, embodiments of the invention are not limited thereto.

FIG. 3 is a cross-sectional view schematically illustrating a system for thermographic nondestructive evaluation according to some embodiments of the present invention. Referring to FIG. 3, a system 300 may include one or more flash lamps 310 and a thermal imaging camera 320. The one or more flash lamps 310 may be configured to heat a surface of an object, for example the object 100 of FIGS. 1A and 1B or the object 200 of FIGS. 2A and 2B. In some embodiments, the surface of the object 200 may be heated from a room temperature to a temperature that is less than 1° F. above the room temperature. Although embodiments including flash lamps are illustrated, other methods of heating the surface may be used that rapidly heat the surface of the object 200. After the surface of the object 200 is heated, the heat may dissipate into the object 200. The heat may not dissipate in portions of the object 200 that include the defect 210 as quickly as in portions of the object 200 that do not include a defect 210. Thus, a temperature of portions of the surface of the object 200 above the defect 210 may remain at a higher temperature than portions of the surface of the object 200 that are not above a defect 210. The thermal imaging camera 320 may capture a series of thermal images of the surface of the object 200.

Based on the thermal series of thermal images, the defect 210 may be evaluated. For example, the size, shape, and/or depth of the defect 210 may be determined. In some embodiments, sample data may be derived from the series of thermal images, the sample data may be cleaned, a sound zone may be detected, the sample data may be normalized, and the sample data may be compared to simulated and/or previously measured data corresponding to known defects to evaluate the defect 210 of the object 200, as will be described in more detail.

In some embodiments, the thermal imaging camera 320 may capture the temperature profile of the surface being from just before the flash heating is applied to after the flash, resulting a sufficient quantity of images. For example, in some embodiments, the thermal imaging camera 320 may capture the temperature profile of the surface being examined at a rate of about 60 frames per second from just before the flash heating is applied to about 11 seconds after the flash, resulting in about 900 images. The image resolution of the camera 320 may be of the order of 320×256 pixels and defect locations may be revealed as temperature (brightness) contrast that appear in some of the series of images obtained over the time period. In addition to the contrast introduced by the defects, other extraneous noise may also invariably be present in these images. The extraneous signals may include one or more of:

(1) "Salt and pepper" type noise introduced by randomly distributed defective sensor element within a sensor array within the camera 320, which may result in noise amplitudes several times the defect related contrast seen in these images;

(2) Minor variations in the sensitivity of adjacent sensor elements;

(3) Non-uniform temperature indication or vignetting; and/or (4) low level random noise signal from the sensor and electronics.

One or more of these extraneous signals may be present in all 900 frames. Therefore, all of the images may be individually processed to minimize the effect of these extraneous signals, so that the temperature contrast resulting from the presence of defect can be quantified. In addition to the thermal images of the surface at any given time, it may be also possible to plot the variation of temperature at any point (pixel) on the surface as a function of time to indicate a rate of thermal diffusion. This temperature versus time graph corresponding to a fixed position may also be subjected to the low level random noise signal mentioned above.

FIG. 4 is a plan view schematically illustrating an object including defects according to some embodiments of the present invention. Referring to FIG. 4, an object 400 may include one or more defects 430. The defects 430 may not be uniform. For example, the defects 430 may include various sizes, shapes, and or depths from the surface of the object 400. The surface of the object 400 may be heated using, for example, the one or more flash lamps 310 illustrated in FIG. 3. In some embodiments, the surface may not be heated uniformly. For example, the heating of the surface may include vignetting. Moreover, an area 410 may surround a heated area 420 of the surface, and may not be heated as much as the heated area 420.

Minimizing the Effects of Vignetting in the Thermographic Data

In some embodiments, the thermographic data may be processed to minimize the effects of non-uniformity, or vignetting. A first step of the processing may consider correction for pre-flash temperature. For example, thermograoghy may include finding the temperature rise of the frames individually. FIGS. 5A and 5B are graphs illustrating a one dimensional array of temperature difference data of pixels of one frame, according to some embodiments of the present invention. Referring to FIGS. 5A and 5B, an array of pixel data of a frame may be reordered as a one dimensional array in which the pixel numbers are assigned in ascending order proportional to $\Delta T$, the temperature difference from the minimum temperature seen in the frame. Such rearranged data is plotted as $\Delta T$ versus ordered pixel number in FIG. 5A and plotted as $\ln(\Delta T)$, the logarithm of the temperature difference, in FIG. 5B.

In these figures, pixels may be categorized into three distinct regions based on the values. A first region may represent a group of pixels having the lowest temperature differences. These pixels may correspond to the area 410 along the periphery of the heated area 420 of the object 400 of FIG. 4. Since this is an artifact, some embodiments may include excluding these pixels from further consideration. A second region may include a majority of the pixels in the frame that may fall within a narrow band of $\Delta T$ values. These pixels may correspond to the portions of the area 420 of FIG. 4 that do not include the defects 430. Ideally most of these pixels should have the same $\Delta T$ values except the ones that are located in the periphery of defects if only a small area of the specimen that has defects. The temperature variation among these pixels may be caused by vignetting. The temperature difference within this group of pixels may correspond to the temperature difference from the periphery to the center of the frame. The exact number of these pixels may be narrowed down through an iterative process and/or by comparing the rearranged temperature differences of a few randomly selected frames. Identification of these pixels may serve two important purposes. The first one is to individually evaluate the level of vignetting seen in a frame. For this purpose, the pixel numbers within the second region may be reverted back to their x and y location to indicate their original positions and may be fitted with a paraboloid to determine and compensate for the level of spurious vignetting found. The second important use of this classification is the identification of a group of points on the surface that could be used as reference points to compare with defective regions to obtain temperature profiles that will quantify the defect diameter and depth. The remaining region of pixels, with higher temperature differences, may correspond to the defects 430 of FIG. 4.

To minimize the effect of vignetting, a symmetric 1st or 2nd order surface may be fitted using a regression method for the data corresponding to the second region. FIG. 6 is a graph of a surface fitted to temperature difference data of a second region according to some embodiments of the present invention. Referring to FIG. 6, non-uniformity or vignetting may me minimized using an appropriate bivariate function. For example, in some embodiments, a first order bivariate function may be used to minimize non-uniformity. In some embodiments, an equation of the surface may be given by:

$$z = a_1 x^4 y^4 + a_2 x^4 y^2 + a_3 x^4 + a_4 x^2 y^4 + a_5 x^2 y^2 + a_6 x^2 + a_7 y^4 + a_8 y^2 + a_9$$

The average of the data (surface) may be given by:

$$z_{av} = \Sigma(z)/n*m$$

The image resolution may be n×m. The corrected temperature ($T_{corr}$) data may be calculated from the original temperature data T:

$$T_{corr} = T - (z - z_{av})$$

FIG. 7 is a graph illustrating pixel data before and after correcting for vignetting according to some embodiments of the present invention. Referring to FIG. 7, both the second region and the third region of pixel data may be corrected for non-uniform heating. Before correction for vignetting, along a one dimensional slice, pixels in the second region may deviate from an average value in roughly a paraboloid shape. The pixel values may also include a higher frequency random noise. Pixels with values that deviate greatly from the paraboloid shape may be pixels in the third region, or in other words, pixels corresponding to defects. After correcting for vignetting, pixel values corresponding to the pixels of the second region include less deviation from an average value and may not follow a paraboloid shape.

Data Smoothing

After compensating for non-uniform heating, a data smoothing operation may be done on pixels of frames starting from a selected first stable frame. The selected first stable frame may be selected after skipping several initial frames to eliminate effects of the flash. Although particular data smoothing operations may be described according to some embodiments, other embodiments may include different smoothing operations or may include data smoothing operations in a different order from those described.

According to some embodiments, first, the data may be filtered for salt and pepper noise and image wise smoothened for each time frame:

a) Thermographic data and time may be converted to natural logarithmic scale (ln(t) and ln($\Delta$T));

b) An initial stable frame may be selected based on the raw data, all time frames before the selected initial stable frame bay be excluded;

c) A new time scale may be created that is equally divided in the logarithmic domain from the first original time step to the last;

d) Using the acquisition time and data, splines may be fitted per pixel for the newly created time scale described above;

e) The splines may be smoothened with cubic splines for each pixel across the newly created logarithmic time domain;

f) Cubic spline fit filtering may be additionally done on each time frame to smoothen the temperature data on each frame.

Sound Zone Detection

According to some embodiments, a sound zone may be detected. The sound zone may be an area that does not include defects. The temperature of the sound zone may always remain lower than the rest of the surface area at any given time. Therefore, it may be possible to trace the temperature profile of pixels which remain lower than the rest of the area at all times to identify the sound zone. This process may be affected by non-uniform heating to a certain extent. The effects of the non-uniform heating may be reduced or eliminated as discussed above before detecting the sound zone. In some embodiments, detecting the sound zone may include selecting a group of pixels that represent the sound zone:

1. A number of time frames may be selected;
2. For each of the selected time frames, the effects of vignetting may be minimized as described above; and
3. A predetermined number of pixels within the second region may be selected to represent the sound zone.

The predetermined number of pixels may be selected based on the pixel values in the selected time frames. For example, in some embodiments, the predetermined number of pixels may be selected from within a middle of the second region (See FIGS. 5A and 5B). In some embodiments, the predetermined number of pixels may be selected using the derivative of the temperature delta values of the pixels. For example, the predetermined number of pixels may be selected where the derivative of the values is approximately zero.

It may not be necessary to select all pixels within the sound zone. For example, only a subset of the second region of pixels may be selected, which may reduce the amount of computation necessary. If a proportion of the area of the defects to an area of the region not including defects is higher, the number of pixels which correspond to the second region may decrease. If the defect region is higher to the extent that the detection of sound zone becomes difficult, a stitched data obtained across the test object can be used.

Background of Temperature Decay

FIGS. 8A, 8B, and 8C are graphs illustrating measured pixel temperature values versus time according to some embodiments of the present invention. FIG. 8A illustrates the logarithm of temperature difference values of a pixel, ln($\Delta$T), versus the logarithm of time, ln(t). Values corresponding to a pixel in a defect free zone (second region, sound zone) are illustrated with a solid line. Values corresponding to a pixel in a defected zone (third region) are illustrated with a dashed line. The illustrated values are exemplary and are not intended to limit the scope of the invention. In some embodiments, measured values may be different from those illustrated. The illustrated values FIG. 8B illustrates the first derivative of the values of FIG. 8A. FIG. 8C illustrates the second derivative of the values of FIG. 8A. Referring to FIGS. 8A, 8B, and 8C, in a defect free zone, temperature differences of a pixel may decrease in a relatively constant logarithmic decay until a break time and then remain relatively constant at an equilibrium temperature, or saturation temperature difference.

The variation of surface temperature of a semi-infinite solid as a function of time, after the surface is subjected to an instantaneous rise in temperature such as in flash heating, may be represented by the formula:

$$\Delta T = \frac{q_0}{\varepsilon\sqrt{\pi t}}$$

where $\Delta T = T - T_0$, which is the difference between the temperature T at any time t after the flash and the initial temperature $T_0$ of the surface before the flash, where q0 is the total heat supplied at the boundary as a flash and where $\varepsilon$ is the effusivity. The effusivity may be represented by the formula:

$$\varepsilon = \sqrt{\kappa \rho c}$$

where $\kappa$ is thermal conductivity, $\rho$ is density, and c is heat capacity of the solid. In a semi-infinite body, following the flash that instantaneously raises the temperature of the surface of the semi-infinite body, the surface temperature keep decreasing according to the relationship given above. However, for a slab with a finite thickness, L, the evolution of T may be represented by the formula:

$$\Delta T = \frac{q_0}{L\rho c}\left\{1 + 2\sum_{i=1}^{\infty} e^{\left(-\pi^2 i^2 \frac{\alpha t}{L^2}\right)}\right\}$$

where $\alpha$ is the diffusivity of the material which may be represented by the formula:

$$\alpha = \frac{\kappa}{\rho c}$$

The equilibrium temperature, or saturation temperature difference, of the slab may be represented by the formula:

$$\Delta T^* = \frac{q_0}{L\rho c}$$

and a time corresponding to the equilibrium temperature, commonly referred to as break time, t*, may be represented by the formula:

$$t^* = \frac{L^2}{\pi \alpha}$$

For a semi-infinite solid, taking natural logarithm of the equation above for the temperature difference results in the following equation:

$$\ln(\Delta T) = -0.5\ln(t) + \ln\left\{\frac{q_0}{\varepsilon\sqrt{\pi}}\right\}$$

Thus, for the semi-infinite solid, the slope of the plot of ln(ΔT) vs. ln(t) may have a value of −0.5. However, for a finite thickness plate, the temperature may start to level off at a value of ΔT* at a time of t*. As illustrated in FIG. 8B, the slope of the temperature decay of the finite thickness plate may also be −0.5 until the temperature levels off at time t*. As illustrated in FIG. 8C, the time, $t_{bw}$, corresponding to the peak in the second derivative of the defect free zone pixel may correspond to the time, t*, and therefore, may correspond to the thickness, L, of the finite thickness plate. The time, $t_d$, corresponding to the first peak in the second derivative of the defected zone pixel may correspond to a depth of a defect. However, as shown in the formulas above, without normalization parameters corresponding to the composition of the plate may be necessary to determine the depth of the defect.

Normalization Technique

Temperature difference and time data may be normalized with respect to the saturation temperature difference (ΔT*) and characteristic time (or break time, t*). The saturation temperature difference (ΔT*) may be a difference between the measured pixel temperature values and a saturation temperature of the pixel when the temperature has stabilized. This method of normalization may facilitate comparison of experimental and numerical data without requiring knowledge of thermal material properties of the evaluated object. The temperature difference may be normalized as a normalized temperature difference, $\Delta T_n$, which may correspond to the temperature difference, ΔT, divided by the saturation temperature difference, ΔT*.

FIGS. 9A, 9B, and 9C are graphs illustrating normalized measured pixel temperature values versus normalized time according to some embodiments of the present invention. FIG. 9A illustrates the logarithm of normalized temperature difference values of a pixel, $\ln(\Delta T_n)$, versus the logarithm of normalized time, $\ln(t_n)$. Values corresponding to a pixel in a defect free zone (second region, sound zone) are illustrated with a solid line. Values corresponding to a pixel in a defected zone (third region) are illustrated with a dashed line. The illustrated values are exemplary and are not intended to limit the scope of the invention. In some embodiments, measured values may be different from those illustrated. The illustrated values FIG. 9B illustrate the first derivative of the values of FIG. 9A. FIG. 9C illustrate the second derivative of the values of FIG. 9A. Referring to FIGS. 9A, 9B, and 9C, in a defect free zone, normalized temperature differences of a pixel may decrease in a relatively constant logarithmic decay until a break time, where t=t*, $t_n=t/t^*=1$, and $\ln(t_n)=0$, and then remain relatively constant at an equilibrium temperature, where ΔT=ΔT*, $\Delta T_n = \Delta T/\Delta T^* = 1$, and $\ln(\Delta T_n)=0$.

From the normalized plot, the defect depth may be estimated directly from the corresponding time, $\ln(t_{nd})$ as a relationship between the defect depth and the thickness of the plate. Thus, a depth of a defect, $l_d$, may be estimated using the formula:

$$l_d = l^*(t_{nd})^{0.5}$$

where l is the thickness of the plate and $t_{nd}$ is the time corresponding to the first peak in the second derivative in the normalized time corresponding to a pixel in a defected zone.

Physics Based Data Generation

In an ideal situation, when a heat pulse is applied at the surface then the heat diffusion in a sound region, until the break time, may be represented as a semi-infinite solid and may decay exponentially with a slope of −0.5 in the logarithmic scale. Therefore, ideally, if a defect free surface sample is given then the 1-D heat diffusion at the very beginning may be represented in logarithmic normalized time as a line that goes through the origin with a gradient of −0.5.

Once the representative pixels for sound zone are found, the physics of diffusion may be used to generate thermal data from almost during the flash point itself. Having the normalized data with respect to the characteristic time (t*) and the saturation temperature difference (ΔT*), the temperature time profile of each pixel may be generated for the initial and end times using the experimental data in a middle region. Another normalized parameter that may be used in this data generation is the depth ratio (rd), which may be defined as the ratio of the depth of defect (ld) to the thickness of the specimen (l).

FIG. 10 is a graph illustrating an ideal heat diffusion shown in normalized form according to some embodiments of the present invention. Referring to FIG. 10, since the representative pixels of sound zones are determined, the normalized data of those representative data may be used to generate reference data to very early and late times. The concept of this theoretical generation of data is that the temperature evolution of pure heat diffusion would be of the form of a semi-infinite solid. In this, for a complete description, $\ln(q_0/e\pi^{0.5})$ should be known or should be calculated from the experimental data. This will be only possible if sound zones are detected successfully. Once the sound zones are detected may be possible to construct the temperature evolution of the sound zones and then connecting all the other data curves to this curve appropriately. It may be possible to have several methods of generating those data. One of them may be assuming spline fits between the experimental data and the beginning of the theoretical data. Standardization may be more universal if it is done in the normalized time and temperature domain. There may be several ways to smoothly connect the experimental data to the theoretically developed data.

FIG. 11 is a graph illustrating an average of sound zone data according to some embodiments of the present invention. Referring to FIG. 11, after selecting a number of pixels to represent the sound zone, an average of the pixel data may be derived as shown in FIG. 11.

Along the curve shown, a point $P_{skp}$ may correspond to the approximate first stable frame. All the points with gradient approximately equal to −0.5 in the logarithmic time may be selected. A threshold value for the gradient can be set for the selection process. For example, all points between points P1 and P2 may have a gradient of approximately −0.5 within the threshold value. Using the selected points, a line (Q1Q2) with a gradient of −0.5 is illustrated. The peak of the second derivative of the average sound zone data may be found, representing the break time (t*). A vertical line at the break time is illustrated (R1R2). An intersection point of this vertical line and the previous line may give the saturation temperature difference (ΔT* at point S). Once ΔT* and t* are known, data may be normalized with respect to these to parameters. It may also be possible to obtain the break time by estimating the saturation temperature difference using the later data of the sound zone. An average temperature of the later temperature difference data may be approximately equal to the saturation temperature difference. An intersection point of a horizontal line at the saturation temperature difference and the line Q1Q2 may give the break time (t*).

Referring again to FIG. 10, logarithmic normalized time data may be created to have a range in $\ln(t_n)$ of −20 to 5. The normalized time data may be divided into normalized time steps of 0.02. A time corresponding to $\ln(t_n)$=−12, may correspond to point A. A time corresponding to $\ln(t_n)$=−11 may correspond to point B. The time values of points A and B may be chosen based on a minimum depth of the defect. For example, with these values, it may be possible to characterize a defect at the depth ratio of $1\times10^{-5}$ (depth ratio being the ratio of the depth to the thickness of the specimen). The frame number corresponding to P1 in FIG. 11 may be identified and may correspond to point D in FIG. 10. A frame corresponding to point C may be selected such that the difference in the logarithmic time between frames C and D is 2 ($\ln(t_n)$=2 between points C and D). A line GH may be a horizontal line through the origin, which may correspond to the saturation temperature (T*). A point F may be defined at $\ln(t_n)$=0.3. All experimental data may be terminated at this point. In other words, experimental data beyond this point in time may not be considered.

An average of the representative sound zone curve may be created in the normalized logarithmic time and temperature domain. This curve may serve as a skeleton for the data processing. To create this curve, early theoretical data, a line with gradient −0.5 going through the origin, may be used as a line AC. Experimental data, smoothed and normalized, from the average of the representative sound zone may be used as a curve DF. Later experimental data, a horizontal line that goes through the origin, may be used as a line GH. These three segments may be connected using a spline to generate data to be used in between and this curve (ACD-FGH) may be the skeleton for the data processing. For example, a mathematical software package, such as MAT-LAB, may be used to generate the data.

Temperature evolution data obtained experimentally may be smoothly connected to the straight line AB, early data, and straight line, GH, later data. While, in some embodiments, this objective could be achieved in number of ways, one such method is described herein.

Point D may be taken as a reference point for deciding on the termination point of experimental data. A margin on $\Delta(\ln(T_n))=\delta\gamma$ may be set based on the experience on the current experimental data. For example, the margin may be selected as δγ=0.4. A point $D_0$ may be defined which is δγ below the reference point D and then a horizontal line may be drawn from Do to meet the base sound zone curve ACGH, a point E. Another margin may be set as δγ1=0.75δγ and δγ2=0.75δγ above and below a point D1 which may be at the same normalized temperature difference as point D and at the same normalized time as point E. These margins may be represented as line E1E2.

All the experimental $\ln(T_n)$ data which goes through the segment E1E2 at the time frame corresponding to point E may be terminated at this time frame. In other words, experimental data after the time frame corresponding to point E for pixels whose normalized experimental data have a value $\ln(T_n)$ at the time frame corresponding to point E between E1 and E2 may not be considered. All the experimental $\ln(T_n)$ data which is less than E2 at the time frame corresponding to point E may be terminated at the time frame corresponding to point D. All other experimental data may be terminated at a time frame corresponding to point I, which may be close to the original skipped frame.

All the data which were terminated at the time frame corresponding to point E or at the time frame corresponding to point D may be smoothly connected with a spline to the line AC. A point C1 may be selected on line AD such that the vertical distance between points I and C1 is equal to δγ. All the data terminated at the time frame corresponding to point I may be smoothly connected with a spline to line AC1.

All the data terminated at point F may be smoothly connected with a spline to line GH. All of the splines may be smoothened using cubic splines.

FIG. 12 is a graph illustrating a sample resultant set of curves with raw normalized experimental data according to some embodiments of the present invention. Referring to FIG. 12, experimental data may be compared with the created data (all blue broken lines are experimental data. FIG. 13 is a graph illustrating a finalized set of curves according to some embodiments of the present invention.

Referring to FIG. 13, a final set of $\ln(\Delta T_n)$ vs. $\ln(t_n)$ curves is illustrated. These normalized curves may be compared to previously obtained normalized experimental and/or calculated data to evaluate a defect.

Correlation Method of Defect Characterization

A correlation method may utilize a data base of numerical models. The models may be compared with an unknown experimental defect feature. All the geometrical parameters of the numerical model may be known. However, it may not be necessary to know these parameters for a real defect. A closest matching numerical model may be approximately equivalent to the real defect. The correlation analysis in the defect identification may include selection of appropriate features for correlation. Contour plots of temperature image or first derivative (1d) or second derivative (2d) or temperature contrast with logarithmic time and profile lengths as axis may be identified to be an appropriate identity for defect identification.

FIG. 14 is a cross-sectional view of an axisymmetrical model according to some embodiments of the present invention. Referring to FIG. 14, to obtain the numerical contour plot, axisymmetric models may be created to represent a particular defect diameter (2r) and defect depth (d) of a model with a total thickness of h. A model may be numerically solved for surface temperature at the top. The data processing technique described above may be used to generate normalized thermal data.

FIGS. 15-17 are three dimensional graphs illustrating contour plots according to some embodiments of the present invention. FIG. 15 is a plot of $\ln(t_n)$ in the vertical axis, location within the profile length of the model in the horizontal axis, and $\ln(\Delta T_n)$ represented as colors. FIG. 16 is a plot of $\ln(t_n)$ in the vertical axis, location within the profile length of the model in the horizontal axis, and the first derivative of $\ln(\Delta T_n)$ represented as colors. FIG. 17 is a plot of $\ln(t_n)$ in the vertical axis, location within the profile length of the model in the horizontal axis, and the second derivative of $\ln(\Delta T_n)$ represented as colors.

Referring to FIGS. 15-17, temperature, 1d, and 2d data may be obtained from the image processing techniques discussed above. These kinds of contour plots may also be obtained for other parameters, such as temperature contrast or contrast slope. For example, data may be collected or calculated as discussed above and then rearranged into the contour plots as shown.

Experimental contour plots may also be obtained for selected profiles with a defect. Another way of representing this contour plot is by matrix. For example, each contour plot may refer to a single matrix of the contour plot. The experimental contour plots may be compared with model contour plots and correlation coefficients may be found by means of which the defect can be characterized. In other words, parameters for an unknown defect may correspond to the known parameters of the closest contour plots found in the model database.

Method of Evaluating Defects

FIG. 18 is a block diagram illustrating steps in methods of evaluating defects according to some embodiments of the present invention. Referring to FIG. 18, sample data may be collected (block 2210). In some embodiments, data may be collected using the system 300 of FIG. 3. Data may be collected by heating the surface of a sample using flash lamps and then recording the temperatures of the surface over a time period using a thermographic camera. Parameters corresponding to a composition of the sample may or may not be known.

The collected sample thermographic data may be cleaned (block 2220). For example, cleaning the data may include noise filtering, reducing effects of vignetting, and/or data smoothing.

A sound zone may be detected (2230). A number of pixels may be selected to represent a sound zone that does not contain defects below the surface. The sound zone detection may include selecting a number of time frames, ordering the pixel data by value, and selecting the pixels based on a first derivative of the ordered pixel data.

The collected sample thermographic data may be normalized (block 2240). Normalizing the data may include determining a saturation temperature difference and a break time for the sound zone. Determining the saturation temperature difference and break time for the sound zone may include creating an average of the data for the representative pixels of the sound zone. Determining the break time for the sound zone may include finding a peak in the second derivative of the average sound zone data. Determining the saturation temperature difference for the sound zone may include selecting time frames wherein the average sound data is within a threshold of a slope of $-0.5$ in the logarithmic domain and finding an intersection of a line a slope of $-0.5$ from the selected time frames and a vertical line corresponding to the break time. The collected sample thermographic data may be normalized based on the determined saturation temperature difference and break time.

In some embodiments, the collected sample thermographic data may be reconstructed using a physics based data reconstruction (block 2250). For example, the collected sample data may be terminated at beginning and end points based on a comparison of values of collected sample thermographic data to a reference curve. The terminated data may be connected to lines representing ideal early and late data of the reference curve using splines. The connected curves may be smoothed with cubic splines. Accordingly, a finalized set of curves may be produced.

The finalized set of curves may be compared to known defects (block 2260). The finalized set of curves may be compared to a database of curves of defects with known parameters. The database of curves may be produced with experimental and/or calculated values. For example, experimental values may be obtained using the operations of blocks 2210-2240 for a sample with known parameters. Calculated values may be produced using data that is calculated based on a model and processed according the operations of blocks 2230-2240.

Comparing the finalized set of curves to the known defects may include finding a closest match within the curves of the database. Parameters for the unknown defect may correspond to the known parameters of the closest match found in the model database.

The finalized set of curves and/or the curves of the database may be represented as contour plots. The contour plots may include plots wherein two of the axis represent normalized logarithmic time and distance across a profile. A third axis may represent normalized logarithmic temperature difference, the first derivative of the normalized logarithmic temperature difference, and/or the second derivative of the normalized logarithmic temperature difference. The third axis may be represented by colors.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the invention.

What is claimed is:

1. A method of thermographic nondestructive evaluation comprising:

heating a portion of a surface of an object from a first surface temperature to a second surface temperature that is greater than the first surface temperature, the portion of the surface of the object comprising a defect zone comprising a defect that is below the surface of the object and comprising a sound zone;

collecting a plurality of thermal images of the portion of the surface of the object, the plurality of thermal images comprising a series of further thermal images that correspond to times at intervals beginning with a first time, the first time being before the portion of the surface of the object is heated;

detecting the sound zone of the portion of the surface of the object by selecting ones of the plurality of thermal images, determining a set of pixels having the lowest temperatures for each of the ones of the plurality of thermal images, and determining the sound zone, wherein pixels of the sound zone comprise temperature differences that are within a threshold in the ones of the plurality of thermal images;

determining a characteristic time corresponding to a time after the heating of the portion of the surface of the object wherein the sound zone of the surface of the object approaches a steady state temperature;

normalizing temperature data of the plurality of thermal images with respect to the characteristic time and the steady state temperature;

detecting the defect zone based on differences between normalized temperature data of pixels of the defect zone and normalized temperature data of pixels of the sound zone; and determining a defect depth, $l_d$, based on a peak in a second derivative of the normalized temperature data in the defect zone at a time, $t_{nd}$, and a known thickness of the object, l, using a relationship of $l_d = l*(t_{nd})^{0.5}$.

2. The method of claim 1, further comprising, based on thermal data contained in the plurality of thermal images, calculating a temperature rise at a plurality of points on the surface by subtracting temperatures at the plurality of points before the heat is applied from subsequent respective temperatures at the plurality of points at a plurality of times after the heat is applied.

3. The method of claim 1, wherein the thermal images comprise a final thermal image that corresponds to a time that is at least two times as long after the portion of the surface is heated as the characteristic time.

4. The method of claim 1, further comprising, after collecting the plurality of thermal images, performing at least one of: noise filtering, reducing effects of vignetting, and/or data smoothing.

5. The method of claim 1, wherein detecting the sound zone further comprises ranking the pixels based on the temperature values, and wherein the pixels of the sound zone comprise temperature differences that are within a threshold ranking in the ones of the plurality of thermal images.

6. The method of claim 1, further comprising reducing effects of vignetting and/or non-uniformity before detecting the sound zone.

7. The method of claim 1, wherein determining the characteristic time comprises determining a peak in a second derivative of a temperature decay of pixels of the sound zone.

8. The method of claim 1, wherein normalizing the temperature data of the plurality of thermal images comprises normalizing time, t, of the temperature data to a normalized time scale, $t_n$, based on the characteristic time, $t^*$, wherein $t_n = t/t^*$.

9. The method of claim 1, wherein normalizing the temperature data of the plurality of thermal images comprises normalizing temperature difference, $\Delta T$, of the temperature data to a normalized temperature difference, $\Delta T_n$, based on a steady state temperature difference, $\Delta T^*$, wherein $\Delta T_n = \Delta T/\Delta T^*$.

10. The method of claim 1, further comprising regenerating temperature data at initial and end times of the normalized temperature data based on an ideal normalized temperature decay.

11. The method of claim 10, wherein the regenerated temperature data at the initial times of the normalized temperature data is based on an ideal linear decay in the sound zone with a slope of −0.5 in a logarithmic scale at the initial times.

12. The method of claim 10, wherein the regenerated temperature data at the end times of the normalized temperature data is based on an ideal constant normalized temperature difference of $\Delta T_n = 1$ at the end times.

13. The method of claim 10, wherein the normalized temperature data of the plurality of thermal images at middle times that was collected is connected to the regenerated temperature data at the initial and end times using splines to generate temperature data at times between the initial times and the middle times and between the middle times and the end times.

14. The method of claim 13, further comprising smoothening the splines using cubic splines to generate a finalized set of normalized temperature data.

15. A method of thermographic nondestructive evaluation comprising:

heating a portion of a surface of an object from a first surface temperature to a second surface temperature that is greater than the first surface temperature, the portion of the surface of the object comprising a defect zone comprising a defect that is below the surface of the object and comprising a sound zone;

collecting a plurality of thermal images of the portion of the surface of the object, the plurality of thermal images comprising a series of further thermal images that correspond to times at intervals beginning with a first time, the first time being before the portion of the surface of the object is heated;

detecting the sound zone of the portion of the surface of the object by selecting ones of the plurality of thermal images, determining a set of pixels having the lowest temperatures for each of the ones of the plurality of thermal images, and determining the sound zone, wherein pixels of the sound zone comprise temperature differences that are within a threshold in the ones of the plurality of thermal images;

determining a characteristic time corresponding to a time after the heating of the portion of the surface of the object wherein the sound zone of the surface of the object approaches a steady state temperature;

normalizing temperature data of the plurality of thermal images with respect to the characteristic time and the steady state temperature;

detecting the defect zone based on differences between normalized temperature data of pixels of the defect zone and normalized temperature data of pixels of the sound zone;

determining a defect depth, $l_d$, based on a peak in a second derivative of the normalized temperature data in the defect zone at a time, $t_{nd}$, and a known thickness of the object, l, using a relationship of $l_d = 1*(t_{nd})^{0.5}$; and matching the normalized temperature data with a known numerical model to determine parameters of the defect of the object based on known parameters of a defect of the known numerical model.

16. The method of claim 15, wherein matching the normalized temperature data comprises determining a closest match between the normalized temperature data and a plurality of numerical models that are stored in a database.

17. The method of claim 16, wherein matching the normalized temperature data comprises comparing first and/or second derivatives of the normalized temperature data to the plurality of numerical models.

18. The method of claim 17, wherein the numerical models that are stored in the database are derived from normalized experimental temperature data that is generated from thermographic evaluation of known defects comprising known parameters that are in experimental objects.

19. The method of claim 15, wherein the parameters include normalized depths and widths of the respective defect.

* * * * *